(12) United States Patent
Hodgkins et al.

(10) Patent No.: US 11,305,264 B2
(45) Date of Patent: Apr. 19, 2022

(54) MANUFACTURING HYDROCRACKING CATALYST

(71) Applicants: Saudi Arabian Oil Company, Dhahran (SA); JGC Catalysts and Chemicals Ltd., Tokyo (JP); Japanese Cooperation Center Petroleum (JCCP), Tokyo (JP)

(72) Inventors: Robert Peter Hodgkins, Dhahran (SA); Omer Refa Koseoglu, Dhahran (SA); Koji Uchida, Tokyo (JP); Tomoyasu Kagawa, Tokyo (JP); Mitsunori Watabe, Tokyo (JP)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/569,550

(22) Filed: Sep. 12, 2019

(65) Prior Publication Data

US 2021/0077985 A1 Mar. 18, 2021

(51) Int. Cl.

| B01J 29/06 | (2006.01) |
|---|---|
| B01J 29/08 | (2006.01) |
| B01J 6/00 | (2006.01) |
| B01J 35/00 | (2006.01) |
| B01J 35/10 | (2006.01) |
| B01J 37/30 | (2006.01) |
| C10G 47/16 | (2006.01) |
| B01J 29/12 | (2006.01) |
| B01J 29/89 | (2006.01) |
| B01J 29/16 | (2006.01) |
| B01J 37/00 | (2006.01) |
| B01J 29/10 | (2006.01) |
| B01J 29/14 | (2006.01) |
| B01J 37/02 | (2006.01) |
| C10G 49/04 | (2006.01) |
| C10G 49/08 | (2006.01) |
| C10G 47/14 | (2006.01) |
| C10G 49/06 | (2006.01) |

(52) U.S. Cl.
CPC .......... *B01J 29/084* (2013.01); *B01J 6/001* (2013.01); *B01J 29/08* (2013.01); *B01J 29/088* (2013.01); *B01J 29/106* (2013.01); *B01J 29/126* (2013.01); *B01J 29/146* (2013.01); *B01J 29/166* (2013.01); *B01J 29/89* (2013.01); *B01J 35/006* (2013.01); *B01J 35/1023* (2013.01); *B01J 37/0009* (2013.01); *B01J 37/0201* (2013.01); *B01J 37/30* (2013.01); *C10G 47/14* (2013.01); *C10G 47/16* (2013.01); *C10G 49/04* (2013.01); *C10G 49/06* (2013.01); *C10G 49/08* (2013.01); *B01J 2029/081* (2013.01); *B01J 2229/16* (2013.01); *B01J 2229/183* (2013.01); *B01J 2229/20* (2013.01); *B01J 2229/34* (2013.01); *B01J 2229/37* (2013.01); *C07C 2529/10* (2013.01); *C07C 2529/12* (2013.01); *C07C 2529/14* (2013.01); *C07C 2529/16* (2013.01); *C07C 2529/89* (2013.01); *C10G 2300/70* (2013.01)

(58) Field of Classification Search
CPC .... B01J 2029/081; B01J 29/08; B01J 29/084; B01J 29/088; B01J 29/106; B01J 29/126; B01J 29/146; B01J 29/166; B01J 29/89; B01J 2229/42; B01J 2229/37; B01J 2229/16; B01J 2229/18; B01J 2229/183; B01J 2229/186; B01J 2229/20; B01J 35/1023; B01J 37/0009; B01J 37/0201; B01J 37/30; C10G 2300/70; C10G 47/14; C10G 47/16; C10G 47/18; C10G 47/20; C10G 49/04; C10G 49/06; C10G 49/08; C07C 2529/10; C07C 2529/12; C07C 2529/14; C07C 2529/16; C07C 2529/89
USPC ............ 502/60, 63, 64, 66, 79, 86; 423/700, 423/713, 714
See application file for complete search history.

(56) References Cited

U.S. PATENT DOCUMENTS

| 3,329,481 A | 7/1967 | Arthur | |
|---|---|---|---|
| 3,411,874 A | 11/1968 | Julius | |
| 4,358,397 A | 11/1982 | Chu | |
| 4,438,215 A | 3/1984 | Dessau et al. | |
| 4,698,322 A * | 10/1987 | Santilli | .................... B01J 29/62 502/74 |
| 5,057,203 A * | 10/1991 | Chu | ..................... C10G 35/065 208/46 |
| 5,411,724 A * | 5/1995 | Beyer | ................... C01B 39/026 423/328.2 |
| 5,690,810 A * | 11/1997 | Lawrence | ............ C10G 35/095 208/120.15 |

(Continued)

FOREIGN PATENT DOCUMENTS

| EP | 1253182 | 11/2004 |
|---|---|---|
| EP | 2468401 | 6/2012 |
| WO | WO 88/01254 | * 2/1988 |

OTHER PUBLICATIONS

Shimada et al., "Design and development of Ti-modified zeolite-based catalyst for hydrocracking heavy petroleum," Catalysis Today, Mar. 2009, 141(1-2):43-51.

(Continued)

*Primary Examiner* — Elizabeth D Wood
(74) *Attorney, Agent, or Firm* — Fish & Richardson P.C.

(57) ABSTRACT

A method including subjecting an ultra-stable Y-type zeolite having a low silica-to-alumina molar ratio (SAR), such as in a range of 3 to 6, to acid treatment and heteroatom incorporation contemporaneously to give a framework-modified ultra-stable Y-type zeolite.

23 Claims, 3 Drawing Sheets

(56) References Cited

U.S. PATENT DOCUMENTS

| | | | |
|---|---|---|---|
| 7,700,005 B2* | 4/2010 | Inui | C01B 3/382 |
| | | | 252/373 |
| 8,002,970 B2 | 8/2011 | Euzen et al. | |
| 9,221,036 B2 | 12/2015 | Koseoglu et al. | |
| 9,499,403 B2* | 11/2016 | Al-Muhaish | B01J 35/1038 |
| 9,512,371 B2* | 12/2016 | Abe | B01J 23/883 |
| 2011/0120910 A1* | 5/2011 | Simon | C10G 45/64 |
| | | | 208/60 |
| 2011/0132804 A1* | 6/2011 | Stevenson | B01J 29/047 |
| | | | 208/65 |
| 2012/0085601 A1* | 4/2012 | Oyama | B60T 13/12 |
| | | | 188/151 R |
| 2013/0313164 A1 | 11/2013 | Shu et al. | |
| 2015/0375218 A1* | 12/2015 | Koseoglu | C10L 1/06 |
| | | | 208/120.1 |
| 2016/0051972 A1* | 2/2016 | Koseoglu | B01J 37/0201 |
| | | | 208/111.1 |
| 2019/0022630 A1* | 1/2019 | Koseoglu | B01J 29/166 |

OTHER PUBLICATIONS

PCT International Search Report and Written Opinion in International Appln. No. PCT/US2020/050299, dated Nov. 27, 2020, 15 pages.

* cited by examiner

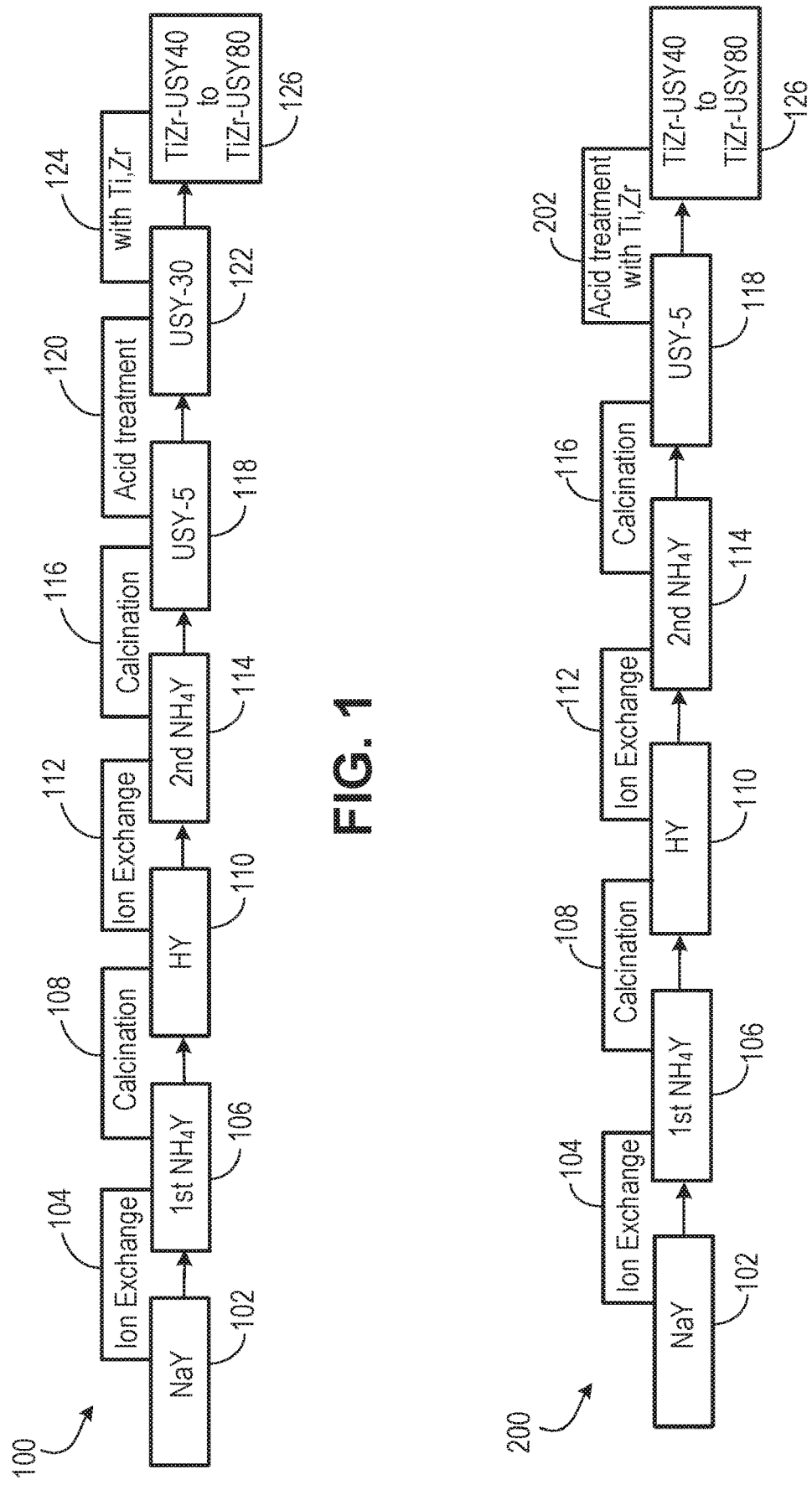

MANUFACTURING HYDROCRACKING CATALYST

TECHNICAL FIELD

This disclosure relates to manufacturing hydrocracking catalyst having a zeolite.

BACKGROUND

Hydrocracking is a catalytic cracking technique assisted by the presence of hydrogen gas. Hydrocracking plants may process feedstocks of different characteristics to produce a range of products. The hydrocracking utilizes hydrogen to break carbon-carbon bonds in the feedstock. Heavy aromatic feedstock may be converted into lighter products in the presence of hydrogen and catalyst. Example feedstocks include heavy fractions of petroleum, such as vacuum gas oil. Example products from hydrocracking are jet fuel and diesel. Hydrocracking may convert high-boiling constituent hydrocarbons in petroleum crude oils to more valuable lower-boiling products, such as gasoline, kerosene, jet fuel, and diesel oil. The hydrocracking may occur in a hydrogen-rich atmosphere at temperatures, for example, in a range of 250° C. to 800° C. and at pressures, for example, up to 200 kilogram per square centimeter ($kg/cm^2$). The presence of hydrogen in the hydrocracking reactor may reduce tar formation, reduce impurities, and reduce buildup of coke on the catalyst, as well as convert hydrogenate sulfur and nitrogen compounds in the feedstock to hydrogen sulfide and ammonia, respectively. Thus, the hydrocracking products may be substantially free of sulfur and nitrogen impurities and consist primarily of paraffinic or saturated hydrocarbons.

The products of the hydrocracking may depend on reaction conditions, such as temperature, pressure, liquid hourly space velocity, and catalyst type and activity. The hydrocracking implemented may depend on the nature of the feedstock and the relative rates of the two competing reactions of hydrogenation and cracking. The hydrocracking may crack the high-boiling, high molecular-weight hydrocarbons into lower-boiling, lower molecular-weight hydrocarbons (e.g., olefinic and aromatic hydrocarbons) and then hydrogenate the lower molecular-weight hydrocarbons.

SUMMARY

An aspect relates to a method of producing a hydrocracking catalyst for hydrocarbon oil. The method includes exchanging at least 80% of sodium (Na) ions in a Y-type zeolite with ammonium ($NH_4$) ions to convert the Y-type zeolite to an ultra-stable Y-type zeolite having a silica-to-alumina molar ratio (SAR) in a range of 3 to 6. The method includes subjecting the ultra-stable Y-type zeolite to acid treatment and heteroatom incorporation contemporaneously to give a framework-modified ultra-stable Y-type zeolite having an SAR of at least 20 or at least 30. In some implementations, the framework-modified ultra-stable Y-type zeolite may have an SAR of at least 40 or at least 80. The heteroatoms incorporated into a framework of the ultra-stable Y-type zeolite in the heteroatom incorporation include titanium atoms and further include zirconium atoms or hafnium atoms, or both.

Another aspect relates to a method of producing a hydrocracking catalyst. The method includes preparing a suspension of an ultra-stable Y-type zeolite in a liquid. The ultra-stable Y-type zeolite has SAR in a range of 3 to 6. The method includes performing acid treatment on the ultra-stable Y-type zeolite to increase the SAR of the ultra-stable Y-type zeolite. The acid treatment includes adding an acid to the suspension. The method includes adding heteroatoms to the suspension contemporaneous with performing the acid treatment to incorporate the heteroatoms into a framework of the ultra-stable Y-type zeolite to give a framework-substituted ultra-stable Y-type zeolite having an SAR of at least 30 or at least 40. In some implementations, the SAR of the framework-substituted ultra-stable Y-type zeolite may be in range of 35 to 120, or in a range of 40 to 100. Lastly, the method includes impregnating a hydrogenative metal on a catalyst support having the framework-substituted ultra-stable Y-type zeolite.

Yet another aspect relates to a method of forming a framework-modified ultra-stable Y-type zeolite for a catalyst support of a hydrocracking catalyst. The method includes subjecting an ultra-stable Y-type zeolite (having an SAR in a range of 3 to 6) to acid treatment and heteroatom incorporation contemporaneously to give the framework-modified ultra-stable Y-type zeolite having an SAR of at least 20 (e.g., at least 30 or at least 40). The framework-modified ultra-stable Y-type zeolite may have an SAR in a range of 20 to 100 and a specific surface area of at least 600 square meter per gram ($m^2/g$).

The details of one or more implementations are set forth in the accompanying drawings and the description below. Other features and advantages will be apparent from the description and drawings, and from the claims.

BRIEF DESCRIPTION OF DRAWINGS

FIGS. 1-2 are block flow diagrams of respective methods of producing a hydrocracking catalyst for hydrocarbon oil.

DETAILED DESCRIPTION

Figure 3:
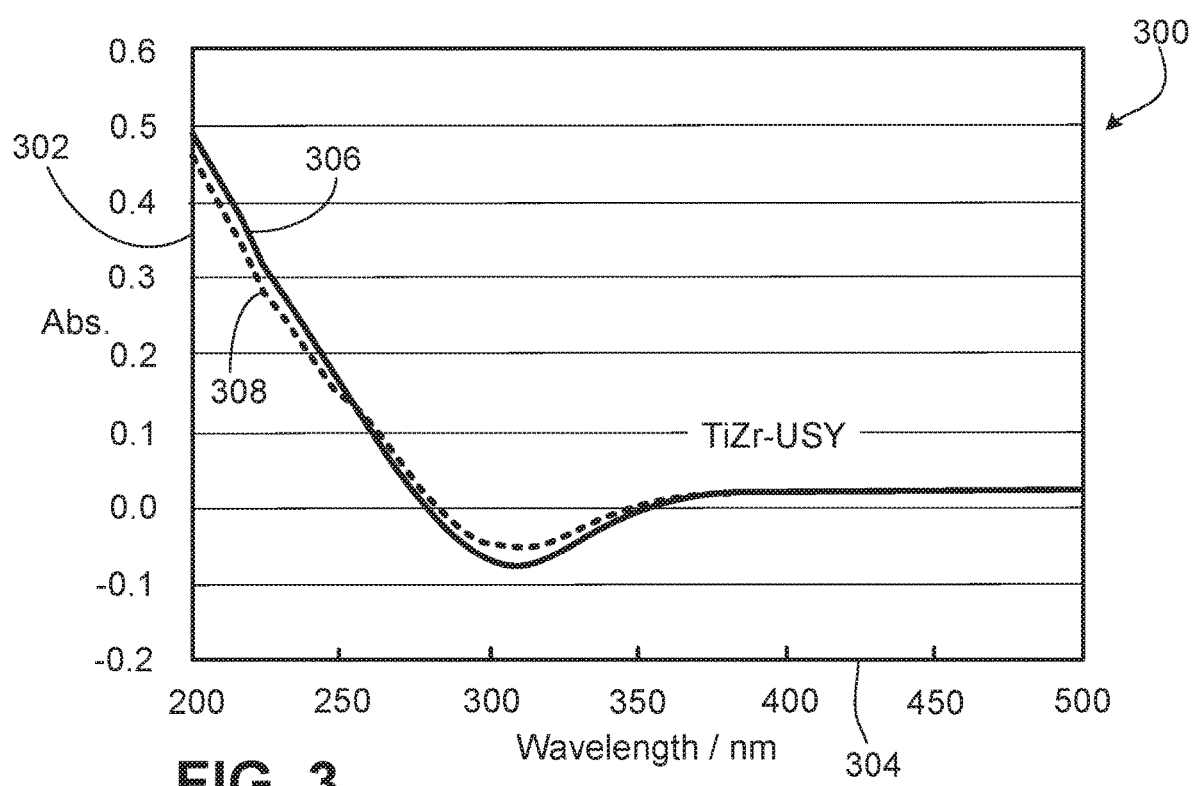
FIGS. 3-4 are an ultraviolet-visible (UV-Vis) spectroscopy plots of absorbance versus wavelength.

Some aspects of the present disclosure are directed to producing a hydrocracking catalyst having a catalyst support that includes a zeolite. Embodiments of the present techniques are directed to manufacturing a hydrocracking catalyst for hydrocracking hydrocarbon oil, such as vacuum gas oil (VGO) and deasphalted oil (DAO). The hydrocracking of the hydrocarbon oil with the present hydrocracking catalyst may give middle distillates (e.g., kerosene and gas oil) or similar compounds. The hydrocracking catalyst may facilitate diffusion of hydrocarbon oils (e.g., VGO and DAO) into mesopores to obtain the middle distillates or similar hydrocarbons.

The present hydrocracking catalyst has a hydrogenative metal and a catalyst support. The catalyst support carries the hydrogenative metal. The catalyst support includes an ultra-stable Y-type zeolite (USY) with a framework having silicon atoms and aluminum atoms constituting the framework. A Y-type zeolite (also labeled as "Y zeolite") typically has a silica-to-alumina molar ratio (SAR) of at least 3. The SAR is the molar ratio of silicon dioxide ($SiO_2$) to aluminum (III) oxide ($Al_2O_3$). The stability of a Y-type zeolite may generally increase as some aluminum ions or sodium ions are removed from the Y-type zeolite to give an ultra-stable Y-type zeolite. An ultra-stable Y-type zeolite has greater stability than the conventional Y-type zeolite. The phrase "ultra-stable Y-type zeolite" is referred to herein as "USY".

The USY framework in the catalyst support of the present hydrocracking catalyst is framework-substituted (framework-modified) in that some of the aluminum atoms constituting the USY framework are substituted (replaced) with titanium atoms, as well as with zirconium atoms or hafnium atoms. Thus, titanium atoms, as well as zirconium atoms or hafnium atoms, or both, form part of the framework to give a USY framework-substituted zeolite. Therefore, the USY in the catalyst support of the present hydrocracking catalyst is referred to herein as a "USY framework-substituted zeolite" or a "USY framework-modified zeolite." The USY in the catalyst support of the present hydrocracking catalyst may also be referred to as a "framework-substituted ultra-stable Y-type zeolite" or a "framework-modified ultra-stable Y-type zeolite."

For the present USY framework-substituted zeolite, aluminum atoms of the USY framework are substituted (replaced) with (I) titanium atoms and zirconium atoms, (II) titanium atoms and hafnium atoms, or (III) titanium atoms, zirconium atoms, and hafnium atoms. Corresponding notations for the USY framework-substituted zeolite may be (I) TiZr-USY, (II) TiHf-USY, or (III) TiZrHf-USY. The substitution may be verified, for example, by ultraviolet-visible (UV-Vis) spectroscopy, near-infrared (NIR) spectroscopy, or Fourier transform infrared (FTIR) spectroscopy.

The titanium atoms in terms of titanium oxide ($TiO_2$) contained in the USY framework-substituted zeolite on a mass basis may be in ranges of 0.1% to 5%, 0.5% to 4%, or 0.6% to 3%. The zirconium atoms or hafnium atoms, or both, in terms of their respective oxides of zirconium oxide ($ZrO_2$) and hafnium oxide ($HfO_2$) may each be contained in the USY framework-substituted zeolite in ranges of 0.1% to 5%, 0.2% to 4%, or 0.3% to 3%. The titanium atom content, the zirconium atom content, and the hafnium atom content of the USY framework-substituted zeolite can be measured, for example, with an X-ray fluorescence analyzer, a high-frequency plasma-emission spectrometer, and an atomic absorption spectrometer.

The Y-type zeolite or USY may give predetermined ranges for certain properties of the USY framework-substituted zeolite. These properties may include, for example, a crystal lattice constant, a specific surface area, and a molar ratio (silica-alumina ratio) of silica (silicon dioxide or $SiO_2$) to alumina (aluminum oxide or $Al_2O_3$). Properties of the USY framework-substituted zeolite are given below. In addition, discussion of these properties, their numerical ranges and verification, testing equipment, and other features are given in U.S. Pat. No. 9,221,036, which is incorporated by reference herein in its entirety for all purposes.

FIG. 1 is a method 100 of producing a zeolite of a hydrocracking catalyst for hydrocarbon oil. The method 100 may synthesize a final USY as a support for the hydrocracking catalyst. The final USY is a USY framework-substituted zeolite, as discussed. The final USY may carry active phase metals in the hydrocracking catalyst. An active phase metal may include a hydrogenative metal. The hydrogenative metal may provide for hydrogenation functionality and additionally other types of functionality.

Initially, a Y-type zeolite (Na—Y) 102 may be subjected to ion exchange 104 for the exchange of sodium ions of the Na—Y 102 with ammonium ions to give a first ammonium-exchanged Y-type zeolite ($NH_4$—Y) 106. An embodiment of the ion exchange 104 includes to add ammonium sulfate to a suspension of the Y-type zeolite (Na—Y) 102 dispersed in water. In some implementations, the resulting solid matter may be: (1) initially washed with water; (2) then washed with an ammonium-sulfate aqueous solution, for example, at a temperature in a range of 40° C. to 80° C.; (3) subsequently washed with water, for example, at a temperature in a range of 40° C. to 95° C.; and (4) then dried at a temperature in a range of 100° C. to 180° C. (typically for at least 30 minutes) to obtain the first $NH_4$—Y 106. In the first $NH_4$—Y 106, 50% to 70% of Na contained in the Y-type zeolite is substituted with $NH_4$ for certain embodiments.

The first $NH_4$—Y 106 may be subjected to calcination 108 to give a HY 110. The HY 110 may be a hydrogen type Y-type zeolite (HY). The calcination 108 may include calcining the first $NH_4$—Y 106 at a temperature, for example, in a range of 500° C. to 800° C. (typically in a saturated vapor atmosphere) for a time in a range of 10 minutes to 10 hours. The output of the calcination 108 may be HY 110. There may remain a substantial amount of Na in the HY 110. Therefore, a second ammonium ion exchange may be performed. The HY 110 may become USY after the ammonium ion exchange and steaming treatment discussed below.

The HY 110 may be subjected to ion exchange 112 to give a second $NH_4$—Y 114 (80% to 97% of Na contained in the Na—Y 102 exchanged with $NH_4$). In some implementations, the ion exchange 112 (additional ammonium-exchanged) can be by: (1) dispersing the HY 110 (as including a mix of protons and Na) in water having a temperature in range of 40° C. to 95° C. to prepare a suspension; (2) adding ammonium sulfate to the suspension and stirring the suspension at a temperature in a range of 40° C. to 95° C. for 10 minutes to 3 hours; (3) washing the solid matter with water having a temperature in a range of 40° C. to 95° C.; (4) next optionally washing the solid matter with an ammonium-sulfate aqueous solution having a temperature in a range of 40° C. to 95° C.; (5) subsequently washing the solid matter with water having a temperature, for example, in a range of 40 to 80° C.; and (6) then drying the solid matter, for example, at a temperature in a range of 100° C. to 180° C. for a time in a range of 30 minutes to 30 hours. The final ammonium ion exchange amount or rate may be 90% or more. In certain instance, the action (4) to wash with ammonium-sulfate solution is not implemented.

The second $NH_4$—Y 114 (ammonium-exchanged Y-type zeolite with 80% to 97% of Na exchanged with $NH_4$) thus obtained may be subjected to calcination 116 to give a USY-5 118, which is a USY having an SAR of 5. In this calcination 116, the second $NH_4$—Y 114 may be calcined, for example, at a temperature in a range of 500° C. to 700° C. (or 550° C. to 650° C.) for a time in a range of 10 minutes to 10 hours (or 30 minutes to 10 hours), for example, in a saturated vapor atmosphere (for example, saturated water vapor). The output of the calcination 116 may be USY-5 118 as having an SAR of about 5. In a particular example, the SAR is 5.2. In other implementations, the output of the calcination 116 may be, for example, USY-3 (SAR of about 3), USY-4 (SAR of about 4), or USY-6 (SAR of about 6). The SAR may be the same or similar as the SAR of the starting Na—Y 102 because the processing 108, 112, and 116 should generally not significantly change the SAR. This is so because the processing actions 108, 112, and 116 do not include acid treatment to target Al atom ejection from the zeolite framework. Lastly, it should be noted that performing the calcination 116 at a temperature outside of the temperature range of 500° C. to 700° C. may reduce the framework substitution amount of heteroatoms (for example, Ti and Zr) incorporated in the subsequent framework-substitution treatment (for example, action 124 in FIG. 1 or action 202 in FIG. 2).

The USY-5 118 is subjected to an acid treatment 120 to increase the SAR to at least 30 to give USY-30 122. The acid dealuminates the zeolite by leaching aluminum atoms to increase the SAR. As the aluminum amount decreases, the SAR may generally increase. To prepare for the acid treatment 120, the USY-5 118 may suspended in water having a temperature, for example, in the range of about 20° C. to 90° C., the range of 20° C. to 30° C., or the range of 15° C. to 35° C., to form a suspension. In one example, the water with the suspended USY-5 has a temperature of at least 60° C. With respect to the concentration of this suspension of the USY-5, the liquid/solid mass ratio may be, for example, in the range of 5 to 15 or in the range of 8 to 12. As for the acid treatment, an inorganic acid or an organic acid may be added to the suspension so that a pH of the suspension is controlled, for example, in a range of to 1.0 to 2.0 or in a range of 0.7 to 2.5. Examples of the inorganic acid that may be added include sulfuric acid, nitric acid, or hydrochloric acid. Examples of the organic acid may be carboxylic acids. The amount of the inorganic acid or the organic acid added is the amount to control the pH of the suspension in a range of 1.0 to 2.0, or 0.7 to 2.5. The amount may be, for example, a 0.5-fold to 4.0-fold molar increase or a 0.7-fold to 3.5-fold molar increase based on an amount of $Al_2O_3$ in the USY-5 118. Lastly, while the USY 122 is denoted as USY-30, an acid treatment 120 can give a greater SAR, for example, in the range of 30 to 100, such as 40 or 80. Thus, the final USY 126 can be USY-40 or USY-80, as depicted, or another SAR.

After completion of the acid treatment 120 that forms the USY-30 122, a separate and subsequent action is heteroatom incorporation 124 to give the final USY 126. The heteroatom incorporation 124 is a framework substitution. The heteroatoms incorporated in the treatment (124) may be Ti and Zr (as depicted) or can be, for example, Ti and Hf (or Ti, Zr, and Hf).

For the heteroatom incorporation 124, a suspension of USY-30 122 may be prepared. Typically, the USY-30 122 is suspended in water to which, for instance, sulfuric acid may be added to the suspension to give a pH of 1.6, for example. Then, a titanium compound may be added to the suspension. In particular, a solution (for example, aqueous solution) having a titanium compound is mixed with the suspension of the USY-30 122. The aqueous solution added also has a zirconium compound or a hafnium compound, or both. The mixture (mixed solution) of the aqueous solution and suspension is neutralized (for example, to pH 7.0 to 7.5) and dried, for instance, at a temperature in a range of 80° C. to 180° C. to give the final USY 126. Before drying, the mixture is typically filtered and then washed with water.

The titanium compound added to the suspension may be titanium sulfate, titanium acetate, titanium chloride, titanium nitrate, and titanium lactate. The amount of the titanium compound added to the suspension may be 0.1° A to 5% by mass (or 0.2% to 4% by mass) on an oxide basis with respect to the USY-30 122. The addition of the titanium compound in an amount of less than 0.1% by mass may result in an insignificant change to the properties of the solid acid sites of the zeolite. The addition of the titanium compound in an amount exceeding 5% by mass may cause clogging of pores of the zeolite.

Examples of the zirconium compound in the added aqueous solution mixed with the suspension include zirconium sulfate, zirconium nitrate, zirconium chloride, and the like. The amount of the zirconium compound added may be 0.1% to 5% by mass (or 0.2% to 4% by mass) on a zirconium oxide basis with respect to USY-30 122. The addition of the zirconium compound in an amount of less than 0.1% by mass may fail to improve solid acid of the zeolite. The addition of the zirconium compound in an amount exceeding 5% by mass may cause clogging of pores of the zeolite.

Examples of the hafnium compound if included in the added aqueous solution added to the suspension are hafnium chloride, hafnium nitrate, hafnium fluoride, hafnium bromide, hafnium oxalate, and the like. The amount of the hafnium compound added is 0.1% to 5% by mass (or 0.2% to 4% by mass) on a hafnium oxide basis with respect to the USY-30 122. The addition of the hafnium compound in an amount of less than 0.1% by mass may not improve a solid acid of the zeolite. The addition of the hafnium compound in an amount exceeding 4% by mass may increases cost of the catalyst.

For the titanium compound, zirconium compound, and hafnium compound (if added), a respective initial aqueous solution of each may be prepared by dissolving each compound in water. The respective initial aqueous solutions may be combined to form the aqueous solution added to the suspension of the USY-30 122.

The pH of the suspension may be controlled in advance, for example, at less than 2.0, or in the range of 1.0 to 2.0, for the purpose of preventing or reducing precipitation occurring during the mixing of the aqueous solution of the titanium compound and zirconium compound (or hafnium compound) with the suspension of the USY-30 122. In some implementations, the aqueous solution is added gradually to the suspension of the USY-30 122. After addition of the aqueous solution to the suspension, the resulting solution may be mixed by stirring at room temperature (for instance, 25° C. to 90° C.) for a time, for example, in the range of 3 hours to 5 hours. After mixing, the mixed solution may be neutralized by adding an alkali (for example, aqueous ammonia) so that a pH of the mixed solution is controlled to a pH in a range of 7.0 to 7.5 and to give the final USY 126. The resulting framework-substituted zeolite (final USY 126) may be filtered, washed with water, and dried at a temperature in a range of 80° C. to 180° C. to give the final USY 126. The final USY 126 is a USY framework-substituted zeolite, as discussed.

The final USY 126 as a framework-substituted zeolite may be TiZr-USY in which titanium atoms and zirconium atoms are substituted for some of the aluminum atoms forming the framework of the ultra-stable Y-type zeolite. The final USY 126 as a framework-substituted zeolite may be TiHf-USY in which titanium atoms and hafnium atoms are substituted for some of the aluminum atoms forming the framework of the ultra-stable Y-type zeolite. The final USY 126 as a framework-substituted zeolite may be TiZrHf-USY in which titanium atoms, zirconium atoms, and hafnium atoms are substituted for some of the aluminum atoms forming the framework of the ultra-stable Y-type zeolite. In some implementations, the final USY 126 may be TiZr-USY40 (SAR=40) or TiZr-USY80 (SAR=80), as depicted in FIG. 1. With increasing acid concentration, mixing time and temperature, followed by washing, more Al may be ejected from the framework of the zeolite, which may result in an increase in SAR from 30 to 40 or 80. The heteroatom incorporation 124 in method 100 is performed on a USY having an SAR greater than 20, or at least about 30, such as with USY 122.

FIG. 2 is a method 200 of producing a hydrocracking catalyst for hydrocarbon oil. The method 200 may synthesize a final USY 126 as a support for the hydrocracking catalyst in accordance with embodiments of the present techniques. The final USY 126 is a USY framework-substituted zeolite, as discussed. The final USY 126 may carry an active phase metal in the hydrocracking catalyst. The active phase metal may be a hydrogenative metal that gives hydrogenation functionality. In addition to hydrogenation functionality, the hydrogenative metal may also have hydrodesulfurization functionality and hydrodenitrogenation functionality.

The method 200 may perform similar or same (identical) actions 104, 108, 112, and 116 of method 100 depicted in FIG. 1. However, the separate actions of acid treatment 120 and heteroatom incorporation 124 of method 100 are combined and performed together contemporaneously in method 200. In that respect, method 200 is different than method 100.

In method 200 (as in method 100), a Y-type zeolite (Na—Y) 102 may be subjected to ion exchange 104 for the exchange of sodium ions with ammonium ions to give a first ammonium-exchanged Y-type zeolite (NH$_4$—Y) 106. The ion exchange 104 may be as described for method 100.

In method 200 (as in method 100), the first NH$_4$—Y 106 may be subjected to calcination 108 to give a HY 110 that is a hydrogen type Y-type zeolite (HY). The calcination 108 may be as described for method 100.

In method 200 (as in method 100), the HY 110 may be subjected to ion exchange 112 to give a second NH$_4$—Y 114 (80% to 97% of Na contained in the Na—Y 102 exchanged with NH$_4$). The ion exchange 112 may be as described for method 100.

In method 200 (as in method 100), the second NH$_4$—Y 114 (ammonium-exchanged Y-type zeolite with 80% to 97% of Na exchanged with NH$_4$) may be subjected to calcination 116 to give a USY-5 118, which is a USY having an SAR of 5. The calcination 116 may be as described for method 100.

In contrast to method 100, the USY-5 118 in method 200 may be subjected to a combined operation 202 (simultaneous implementation) of acid treatment-heteroatom incorporation in which the acid treatment (to increase SAR) and the heteroatom incorporation (framework substitution) are performed contemporaneously. Thus, unlike method 100, a USY having an SAR less than 20 (for example, SAR of about 5) is subjected to heteroatom incorporation in method 200. The USY may have am SAR less than 10 when subjected to heteroatom incorporation. The USY-5 118 may be subjected to an acid treatment to increase the SAR to at least 30, at least 40, or at least 80.

The heteroatom incorporation generally does not contribute to the increase the SAR in that the heteroatoms do not alter the SAR. The acid treatment increases SAR. The acid treatment selectively removes Al from the zeolite framework. The heteroatom incorporation may alter acidic properties of the zeolite and enhance yield of oils (for example, diesel oils) in hydrocracking reactions of heavy oils with hydrocracking catalyst having the zeolite as a support.

The acid treatment performed in the combined operation 202 may include the addition of an inorganic acid (for example, sulfuric acid, nitric acid, or hydrochloric acid) or an organic acid (for example carboxylic acids) to a suspension of the USY-5 118 in water to control the pH of the suspension at less than 2.0. During the acid treatment, an aqueous solution may be added to the suspension for the heteroatom incorporation in the combined operation 202. The aqueous solution for the heteroatom incorporation may have a titanium compound (for titanium atoms), as well as a zirconium compound (for zirconium atoms) or a hafnium compound (for hafnium atoms), or both. The aqueous solution and compound amounts added for heteroatom incorporation in method 200 may be the same or similar as the corresponding aqueous solution and compound amounts for heteroatom incorporation described with respect to method 100. In embodiments, the aqueous solution may be added gradually (and contemporaneous with the acid treatment) to the suspension.

The heteroatom incorporation in the combined operation 202 may give titanium atoms and zirconium atoms (as noted in FIG. 2) substituted into the zeolite framework replacing aluminum atoms. In other embodiments, titanium atoms and hafnium atoms (or titanium atoms, zirconium atoms, and hafnium atoms) may be substituted into the zeolite framework, replacing aluminum atoms.

After the addition of both the acid and the aqueous solution, the mixture (mixed solution) of the acid, aqueous solution, and the suspension may be further mixed by stirring at room temperature (for instance, 25° C. to 90° C.), such as for 3 hours to 5 hours. Then, the mixture may be neutralized (for example, to pH 7.0 to 7.5) by adding an alkali, such as aqueous ammonia. The resulting framework-substituted zeolite in the neutralized mixture may be filtered from the mixture, washed with water, and dried at a temperature, for example, in a range of 80° C. to 180° C. to give the final USY 126.

As discussed, the final USY 126 as a framework-substituted zeolite may be TiZr-USY, TiHf-USY, or TiZrHf-USY. In some implementations, the final USY 126 may be TiZr-USY40 (SAR=40) or TiZr-USY80 (SAR=80), as depicted in FIG. 1 and FIG. 2. Lastly, while the USY 126 is denoted as USY-30, the acid treatment and the heteroatom incorporation in the combined operation 202 can give a greater SAR, for example, in the range of 30 to 100, such as 40 or 80. Thus, the final USY 126 can be USY-40 or USY-80.

The final USY 126 or similar USY framework-substituted zeolite for the support of the present hydrocracking catalyst may have a crystal lattice constant (or lattice parameter) in the range of 2.430 to 2.450 nanometers (nm) or in the range of 2.435 nm to 2.445 nm, a molar ratio in the range of 20 to 100 (or the range of 25 to 90) in terms of silicon dioxide ($SiO_2$) to aluminum oxide ($Al_2O_3$), and a specific surface area in the range of 600 square meter per gram (m$^2$/g) to 900 m$^2$/g. Other ranges for the specific surface area include 650 m$^2$/g to 800 m$^2$/g, 200 m$^2$/g to 450 m$^2$/g, and 250 m$^2$/g to 400 m$^2$/g. The specific surface-area value is determined by the Brunauer-Emmett-Teller (BET) technique employing nitrogen adsorption.

The crystallinity may be considered. Crystallinity is typically determined by x-ray diffraction. A particular diffraction peak can be selected and its intensity normalized. Other USY-type zeolites can be analyzed and the diffraction intensity normalized against the standard. If the acid treatment was too aggressive, the structural integrity of the zeolite framework would decrease (more amorphous material being generated), and thus crystallinity would decrease. Hence, if the relative crystallinity is maintained after the acid/heteroatom incorporation treatment, this may confirm that the structure of the zeolite is not only maintained but is maintained at a degree of crystallinity.

The hydrocracking catalyst having the USY framework-substituted zeolite may have pores having a diameter of 600 angstrom (Å) or less. The pores may have a volume in the range of 0.40 milliliter per gram (ml/g) to 0.75 ml/g, or 0.45 ml/g to 0.70 ml/g. The pore volume is determined from pore distribution obtained by calculating and analyzing desorption data of nitrogen by the BJH (Barrett, Joyner, and Halenda) method.

The final USY 126 as a framework-modified zeolite may be mixed with a binder, typically an inorganic oxide, and formed into a desired shape (typically a form of extrudate), which is normally dried and fired to provide a support for the hydrocracking catalyst. This support material may then be impregnated with the hydrogenative metal as an active phase metal, and then dried and fired to afford the end hydrocracking catalyst. Generally, the zeolite (final USY 126) alone before being mixed with the binder it typically not impregnated with the metal. Instead, the zeolite/binder (e.g., extrudate) is impregnated with the metal. Moreover, the use of the term is not limited to hydrogenation functionality but can also include hydrodesulfurization functionality and hydrodenitrogenation functionality. The hydrogenative metal may more generally refer to an active phase metal.

The hydrocracking catalyst having the USY framework-substituted zeolite may carry an amount of the hydrogenative metals in the range, for example, of 0.01% to 40% by mass. In implementations, a catalyst support having the final USY 126 or similar USY framework-substituted zeolite may be impregnated with the hydrogenative metal with an aqueous solution containing the hydrogenative metal and calcining the final USY 126 at a temperature in a range of 400° C. to 650° C., for example, for 10 minutes to 3 hours in air. The hydrogenative metal may include metal components (iron, cobalt, nickel, rhodium, palladium, silver, iridium, platinum, or gold) in group 8 of the long periodic table or metal components (chromium, molybdenum, or tungsten) in group 6, or both. Particular examples of the metal component include combinations of molybdenum or tungsten in group 6 and cobalt or nickel in group 8. Other particular examples include metal components of the platinum group, such as platinum, rhodium, or palladium. In the case of molybdenum, tungsten, cobalt or nickel, an amount may be in a range of 3% to 30% by mass in terms of oxide based on mass of the catalyst. In the case of the platinum group (platinum, rhodium, or palladium), an amount may be, for example, in a range of 0.01% to 2% by mass in terms of metal based on mass of the catalyst.

EXAMPLE

First, 50.0 kilograms (kg) of a Na—Y zeolite having a $SiO_2/Al_2O_3$ molar ratio of 5.2, a unit cell dimension (UD) of 2.466 nm, a specific surface area (SA) of 720 $m^2/g$, and a sodium oxide ($Na_2O$) content of 13.0% by mass was suspended in 500 liters (L) of water having a temperature of 60° C. Furthermore, 14.0 kg of ammonium sulfate was added thereto. The resulting suspension was stirred at 70° C. for 1 hour (hr) and filtered. The resulting solid was washed with water. Thereafter, the solid was washed with an ammonium sulfate solution of 14.0 kg of ammonium sulfate dissolved in 500 L of water having a temperature of 60° C. The washed solid was dried at 130° C. for 20 hr, giving about 45 kg of a Y zeolite ($NH_4\ ^{65}Y$) in which 65% of sodium (Na) contained in Na—Y was ion-exchanged with ammonium ion $NH_4$. The content of $Na_2O$ in $NH_4\ ^{65}Y$ was 4.5% by mass.

The $NH_4\ ^{65}Y$ 40 kg was fired in a saturated water-vapor atmosphere at 670° C. for 1 hr to form a hydrogen-Y zeolite (HY). The HY was suspended in 400 L of water having a temperature of 60° C. Thereafter, 49.0 kg of ammonium sulfate was added thereto. The resulting mixture was stirred at 90° C. for 1 hr and washed with 200 L of water having a temperature of 60° C. The mixture was then dried at 130° C. for 20 hr, thereby affording about 37 kg of a Y zeolite ($NH_4\ ^{95}Y$) in which 95% of Na contained in the initial Na—Y was ion-exchanged with $NH_4$. An amount of 33.0 kg of the $NH_4\ ^{95}Y$ was fired in a saturated water vapor atmosphere at 650° C. for 1 hr, giving about 15 kg of a USY-5.2 having a $SiO_2/Al_2O_3$ molar ratio of 5.2 and a $Na_2O$ content of 0.60% by mass.

Then, the USY-5.2 was subjected to a combined acid treatment and heteroatom incorporation. Initially, 1 kg of the USY-5.2 was suspended in 9.3 L of water having a temperature of 25° C. The following were added to the suspension: 2.3 kg of 25% sulfuric acid by mass, 41 g of 18% zirconium sulfate by mass, and 22 g of 33% titanyl sulfate by mass. The resulting mixture was stirred for 3 hr at room temperature. Thereafter, the pH was adjusted to 7.2 with 15% aqueous ammonia by mass. The mixture was stirred for 1 hr at room temperature and then filtered. The resulting solid was washed with 9.3 L of water and dried at 130° C. for 20 hr, giving about 1 kg of a titanium-zirconium-substituted zeolite (TiZr-USY) having an SAR of 77 and which may be labeled as TiZr-USY-77.

This TiZr-USY-77 is a USY framework substituted zeolite that may be analogous to an example of the final USY 126 discussed above with respect to FIG. 2. The properties of this TiZr-USY-77 prepared in this Example include $TiO2$ content=0.88 weight percent (wt. %), $ZrO2$ content=0.76 wt. %, crystallinity=116%, SAR=77, unit cell dimensions=24.32 Å, and surface area=756 $m^2/g$.

FIG. 3 is an ultraviolet-visible (UV-Vis) spectroscopy plot 300 of absorbance 302 versus wavelength (nm) 304. The UV-Vis spectroscopy of the framework-modified TiZr-USY-77 zeolite prepared in the Example is shown in FIG. 3. The spectra in FIG. 3 show tetrahedral coordination indicating framework substitution.

A broad peak at about 250 nm to 350 nm indicates 6-coordinate Ti species. The heteroatoms (Si, Al, Ti, Zr) in a zeolite are 4-coordinate (in a tetrahedral coordination) with each Si atom bonded to four oxygen atoms. Therefore, because each tetrahedra are corner-sharing (one of the oxygen atoms in one tetrahedra is also bonded to the adjacent tetrahedra), the average composition may be said to be $SiO_2$. Hence, a heteroatom in the framework of the zeolite is 4-coordinate. If a 6-coordinate species is present, then this species cannot be in the framework of the zeolite and is thus in the extra-framework. The peak for a 6-coordinate Ti (or Zr) species comes at about 250 nm to 350 nm (see, for example, 406 in FIG. 4). When no Ti or Zr is present (see, for example, 414 in FIG. 4), there is no peak between 200 nm to 400 nm. A 4-corrodinate species are assigned to peaks below 250 nm.

In FIG. 3, the spectrum 306 is for a sample of the TiZr-USY-77 formed in the Example. The Example was performed in the laboratory. The spectrum 308 is for a sample of TiZr-USY similarly prepared but at industrial scale and in accordance with method 200 of FIG. 2. The spectra 306, 308 are similar and thus demonstrate reliability of scale-up. The spectra 306, 308 are unlike spectra typically observed for six-coordinate peaks indicating extra-framework species (see FIG. 4). The UV-Vis spectra in FIG. 3 are similar to spectrum 410 (FIG. 4) for that of the framework-modified TiZr-USY zeolite (USY-5→TiZr-USY-40) prepared per method 100. The spectra of USY zeolites produced as described in the present application and in accordance with embodiments do not show 6-coordinate $TiO_2$, and are unlike the spectra (for example, 408 in FIG. 4) where the pH during insertion of the heteroatoms is >2.0.

Figure 4:
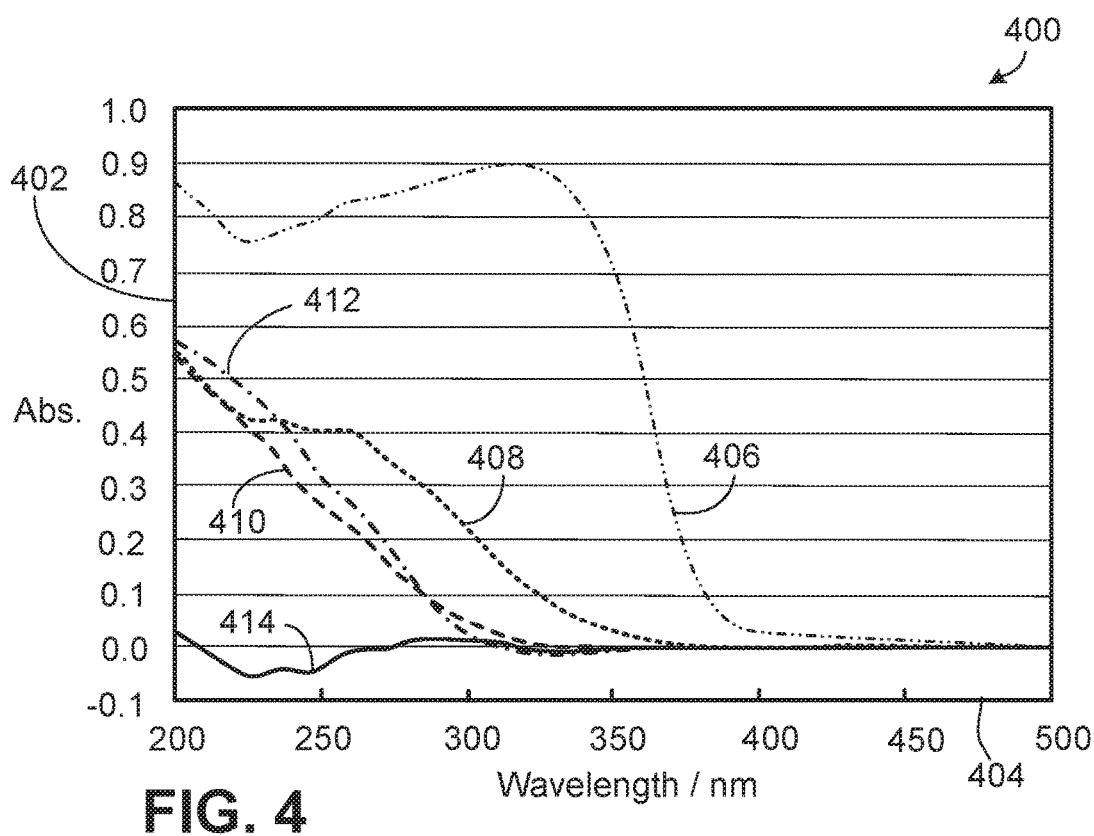

FIG. 4 is a UV-Vis spectroscopy plot 400 of absorbance 402 versus wavelength (nm) 404. The spectrum 406 is for a sample of $TiO2$ (6-coordination). The spectra of the present USY zeolites for the hydrocracking catalyst are different than the spectrum 406 of $TiO2$ (6-coordination). The spectra 408 and 410 are for TiZr-USY-40 (prepared with pH during insertion of the heteroatoms is >2.0) and TiZr-USY-40 (prepared per method 100), respectively, in which the first acid treatment and the contemporaneous second acid treatment and heteroatom incorporation were performed separately with the heteroatom incorporation initiated on USY having an SAR greater than 20 (for example, at least 30). In other words, in particular, the Ti and Zr incorporation was not performed until the acid treatment had increased the USY-5 to USY-30 and requiring a second acid treatment to give the TiZr-USY-40. In contrast, the spectra 412 is for the TiZr-USY-40 per present method 200 in which the USY-5 was subjected to a combined acid treatment/heteroatom (Ti, Zr) incorporation to give the TiZr-USY-40, as discussed above. In the above Example per method 200, the TiZr-USY-40 was labeled as TiZr-USY-77 because the SAR was 77. Lastly, the spectrum 414 is for USY-30 after acid treatment but without Ti, Zr, or Hf heteroatom incorporation. This USY-30 (414 in FIG. 4) is a USY zeolite having a SAR of 30 but with no Ti, Zr, or Hf incorporated.

The USY-5 to TiZr-USY-40 (412 in FIG. 4) is per embodiments (for example, method 200) of the present techniques. Heteroatom incorporation was started on the USY having an SAR of 5 (less than 20). The USY-30 to TiZr-USY-40 (410 in FIG. 4) is per method 100 with the acid treatment at a pH of less than 2.0, as with method 200, but is unlike method 200 in that the heteroatom incorporation was not applied until the SAR was 30 (greater than 20). The spectra 410 and 412 are similar. The USY-30 to TiZr-USY-40 (408 in FIG. 4) is per method 100 with the acid treatment at a pH greater than 2.0 and less effective.

As discussed, titanium atoms, zirconium atoms, and hafnium atoms may be substituted for the aluminum atoms forming a framework of the USY. Thus, the titanium atoms, zirconium atoms, and hafnium atoms may serve as constituents of the framework of the USY. In this respect, "substitution" differs from "carrying" in which atoms or particles of titanium, zirconium, or hafnium are attached to the outside of the framework of the USY. This carrying or attachment to the outside of the framework may be termed as an "extra-framework" species. In the present USY framework-substituted zeolite according to the present invention, additional atoms or particles of titanium, zirconium, or hafnium may optionally be "carried" (or "combined") in the form of, for example, an oxide. When the above particles are present, a particle diameter thereof may be, for example, less than 50 nm. The particle diameters of the titanium particles, zirconium particles, and the hafnium particles carried can be measured from a micrograph taken with a scanning electron microscope (SEM).

For the present hydrocracking catalyst, the support described above contains the USY framework-substituted zeolite and can contain an inorganic oxide. The inorganic oxide above typically contains a substance serving as a granulating agent or a binder. Examples of the inorganic oxide include alumina, silica, titania, silica-alumina, alumina-titania, alumina-zirconia, alumina-boria, phosphorus-alumina, silica-alumina-boria, phosphorus-alum ina-boria, phosphorus-alumina-silica, silica-alumina-titania, and silica-alum ina-zirconia. In one example, the inorganic oxide is primarily alumina or silica-alumina. In implementations, the catalyst support of the present hydrocracking catalyst has the inorganic oxide in ranges of 20% to 98% by mass, or 30% to 80% by mass, and the present USY framework-substituted zeolite in ranges of 2% to 80% by mass, or 20% to 70% by mass.

In some implementations to prepare the support, the USY framework-substituted zeolite is mixed with a binder (for example, the aforementioned inorganic oxide) and formed into a desired shape (for example a form of extrudate), which may be dried and fired to provide the support. This support material may then be impregnated with the hydrogenative metal (mentioned previously), dried, and fired to afford the end hydrocracking catalyst.

Hydrocracking testing to evaluate hydrocracking properties of the catalyst was performed. In particular, a straight-run VGO was contacted in four tests with an example of the present hydrocracking catalyst having a hydrogenative metal and a catalyst support including TiZr-USY-40. The TiZr-USY-40 is a framework-modified zeolite prepared as discussed above with respect to method 200 in FIG. 2. The straight-run VGO had a density at 15° C. of 0.9274 cubic centimeters (cc)/g, an American Petroleum Institute (API) gravity of 21.0° (dimensionless but reported in degrees), and a sulfur concentration of 2.77 part per million by weight (ppmw). The boiling point range of the straight-run VGO is given in Table 1. The boiling point range is per ASTM D86-18 (by ASTM International) entitled "Standard Test Method for Distillation of Petroleum Products and Liquid Fuels at Atmospheric Pressure."

TABLE 1

Boiling-point range of straight-run VGO per ASTM 86

| Property | Boiling Point (° C.) |
|---|---|
| Initial boiling point (IBP) | 266 |
| 10 wt. % | 359 |
| 30 wt. % | 417 |
| 50 wt. % | 457 |
| 70 wt. % | 499 |
| 90 wt. % | 554 |
| 95 wt. % | 577 |

Hydrocracking testing conditions for each of the four tests 1, 2, 3, and 4 were hydrogen (H2) pressure of 135 kg/cm$^2$, a liquid hourly space velocity (LHSV) of 0.5 hr$^{-1}$, and a hydrogen to hydrocarbon ratio of 1000 normalized liters (NL) per L. The temperature of the four tests were: test 1 at 360° C., test 2 at 375° C., test 3 at 390° C., and test 4 at 405° C. Hydrocracking test results are given in Table 2.

TABLE 2

Hydrocracking Test Results

| Test | Relative Conversion (%) | Middle Distillate Selectivity (%) |
|---|---|---|
| 1 | 21 | 100 |
| 2 | 33 | 98 |
| 3 | 60 | 90 |
| 4 | 100 | 84 |

The present hydrocracking catalyst for hydrocarbon oil may be utilized for hydrocracking of high boiling fraction-containing hydrocarbons. The high boiling fraction-containing hydrocarbons mean hydrocarbons in which an amount of fractions having a boiling point of 560° C. or higher accounts for at least 30% by mass. The high boiling fraction-containing hydrocarbons include, for example, VGO and DAO. In the case where hydrocarbon oils, for example, high-boiling-fraction-containing hydrocarbons, are hydrocracked utilizing the hydrocracking catalyst (for hydrocarbon oil) manufactured according to the present techniques, middle distillates can be provided, for example, because of suppression of decomposition of kerosene and gas oil.

The hydrocracking of hydrocarbon oil with the presently-manufactured hydrocracking catalyst may include filling or charging a reactor vessel (for example, a flow reactor) of a hydrocracking system with the hydrocracking catalyst, and treating a hydrocarbon oil. The flow reactor may be a stirring bath reactor, a boiling bed reactor, a baffle-equipped slurry bath reactor, a fixed bed reactor, a rotary tube reactor, or a slurry bed reactor. The hydrocarbon oil subjected to the hydrocracking may be refined oil obtained from crude oil, synthetic crude oil, bitumen, oil sand, shell oil, or coal liquid. The refined oil may be (a) VGO, (b) DAO obtained from a solvent deasphalting process or demetalled oil, (c) light coker gas oil or heavy coker gas oil obtained from a coker process, (d) cycle oil obtained from a fluid catalytic cracking (FCC) process, or (e) gas oil obtained from a visbraking process.

One implementation includes hydrocracking a hydrocarbon oil having a boiling point of 375° C. to 816° C. in the presence of hydrogen at a reactor temperature of 300° C. to 500° C., a hydrogen pressure of 40 kg/cm$^2$ to 300 kg/cm$^2$, a liquid hourly space velocity (LHSV) of 0.1 h$^{-1}$ to 10 h$^{-1}$, and a hydrogen/oil ratio of 500 normal cubic meter (Nm$^3$)/cubic meter (m$^3$) to 2500 N m$^3$/m$^3$. Another implementation of treating a hydrocarbon oil with the present hydrocracking catalyst is treating a hydrocarbon oil having a boiling point of 375° C. to 650° C. in the presence of hydrogen at a reactor temperature of 330° C. to 450° C., a hydrogen pressure of 70 kg/cm$^2$ to 150 kg/cm$^2$, a LHSV of 0.2 h$^{-1}$ to 1.5 h$^{-1}$, and a hydrogen/oil ratio of 1000 Nm$^3$/m$^3$ to 2000 N m$^3$/m$^3$ (for example, to give kerosene and gas oil).

Figure 5:
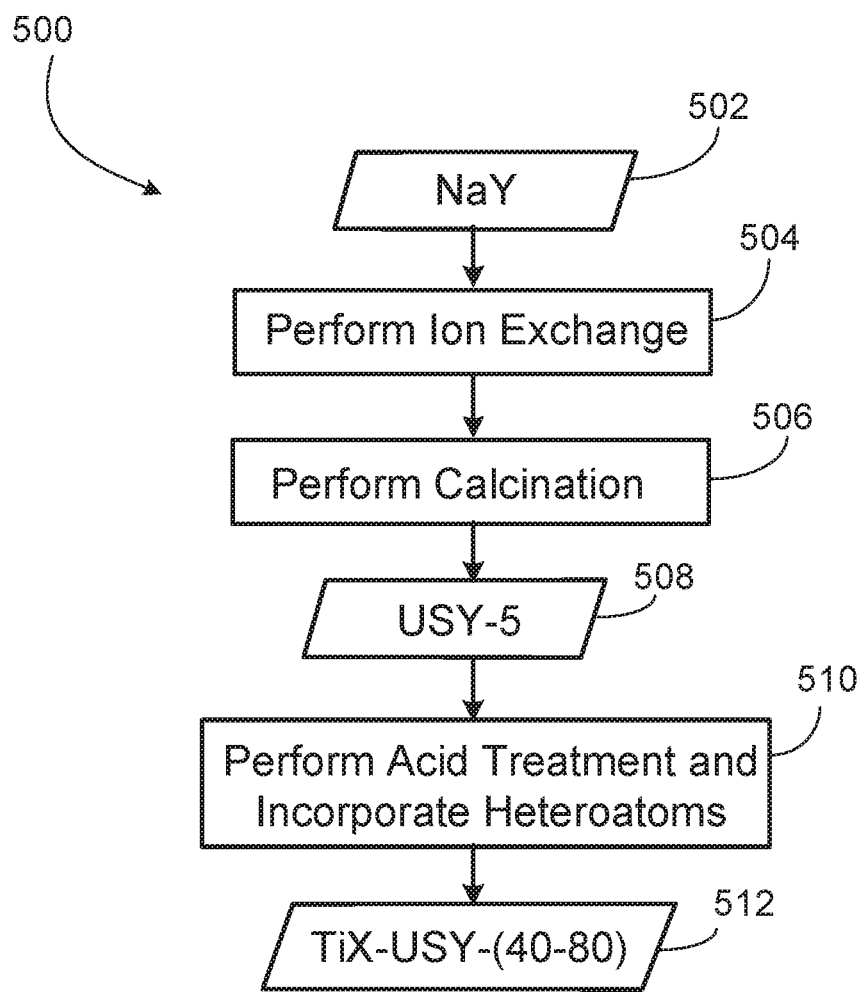
FIG. 5 is a block flow diagram of a method of producing (manufacturing) a hydrocracking catalyst.

FIG. 5 is a method 500 of producing (manufacturing) a hydrocarbon catalyst. A Y-type zeolite (Na—Y) 502 is received. At block 504, the method includes performing ion exchange on the Na—Y 502 to replace sodium ions of the Na—Y 502 with ammonium ions. In one implementation of the ion exchange, ammonium sulfate is added to a suspension of the Na—Y 502 dispersed in water. The solid in the suspension may be washed with water and an aqueous solution of ammonium sulfate, and dried to give Na—Y 502 as ammonium exchanged. The Na—Y 502 as ammonium exchanged may be labeled as an ammonium-exchanged Y-type zeolite or a NH$_4$—Y. The removal of the sodium ions from the Y-type zeolite may increase the stability of the Y-type zeolite. The zeolite may be labeled as an ultra-stable Y-type zeolite (USY) after calcination by steam treatment.

At block 506, the method includes subjecting the Na—Y 502 as ion exchanged to calcination. Calcination may be heating to high temperatures in air or oxygen. In present embodiments, the calcination is heating to high temperatures in saturated vapor such as saturated water vapor. Calcination may be referred to as "firing" or "fired." Calcining may remove unwanted volatiles from a material and convert a material into a more stable, durable, or harder state. In the present method, example conditions of the calcination 506 include temperature in a range of 500° C. to 800° C. for a time in a range of 10 minutes to 10 hours in a saturated water vapor atmosphere.

The performing 504 of an ion exchange and the performing 506 of calcination may be repeated. For example, an ion exchange may be performed at block 504 on the Na—Y 502 and a calcination performed at block 506 on the Na—Y 502 as ion exchanged, ad discussed, to give a first ammonium-exchanged Y-type zeolite. Then, the method may return to block 504 and perform an ion exchange on the first ammonium-exchanged Y-type zeolite to replace additional sodium ions with ammonium ions to give a second ammonium-exchanged Y-type zeolite. The method may proceed to block 506 (a second time) to perform calcination on the second ammonium-exchanged Y-type zeolite to give, for example, the USY-5 508.

In some implementations for the first ammonium-exchanged Y-type zeolite, 50% to 70% of the sodium ions in Na—Y 502 are replaced with ammonium ions. For the second ammonium-exchanged Y-type zeolite, 80% to 97% of the sodium ions in Na—Y 502 are replaced with ammonium ions. Thus, the USY-5 508 (based on the Na—Y 502) may have 80% to 97% of the sodium ions in Na—Y 502 replaced with ammonium ions.

Moreover, whether a single run performance through blocks 504 and 506 or a single repeat iteration as discussed (or multiple repeat iterations), the USY-5 508 may have at least 80% of sodium ions replaced with ammonium ions. Further, the USY-5 508 has an SAR of 5, as indicated by the "-5" notation. However, the SAR of USY 508 may fall in a range of 4 to 6, including USY-4 or USY-6.

In the illustrated embodiment, the method at block 510 performs acid treatment on the USY-5 508 and incorporates heteroatoms into the USY-5 508. The acid treatment and the heteroatom incorporation (framework substitution) are performed contemporaneously. The acid treatment and the heteroatom incorporation increases the SAR. This acid treatment may include the addition of an inorganic acid or an organic acid to a suspension of the USY-5 508 in water to control the pH of the suspension, for example, less than 2.0. During the acid treatment, an aqueous solution may be added to the suspension for the heteroatom incorporation. The aqueous solution may have a titanium compound (for titanium atoms), as well as a zirconium compound (for zirconium atoms) or a hafnium compound (for hafnium atoms), or both. The heteroatoms replace aluminum atoms in (constituting) the framework of the USY-5.

After mixing of the acid and the aqueous solution with the suspension, the mixture may be neutralized (for example, to a pH of about 7) by adding an alkali, such as aqueous ammonia. The resulting USY framework-substituted zeolite in the neutralized mixture may be filtered from the mixture, washed with water, and dried. The USY framework-substituted zeolite may be TiX-USY-(40-80) 512, where X is Zr, Hf, or ZrHf, and the SAR is the range of 40 to 80. The TiX-USY-(40-80) 512 may be included in a catalyst support of a hydrocracking catalyst for hydrocarbon oil.

An embodiment is a method of producing a hydrocracking catalyst for hydrocarbon oil. The method includes exchanging (e.g., via ion exchange and calcination) at least 80% of Na ions in a Y-type zeolite with NH$_4$ ions to convert the Y-type zeolite to an ultra-stable Y-type zeolite having an SAR in a range of 3 to 6 (e.g., at least 5). The method includes subjecting the ultra-stable Y-type zeolite to acid treatment and heteroatom incorporation contemporaneously to give a framework-modified ultra-stable Y-type zeolite having an SAR of at least 20, or at least 30, or at least 40. The framework-modified ultra-stable Y-type zeolite may have an SAR in a range of 20 to 100. In the heteroatom incorporation, the heteroatoms incorporated into a framework of the ultra-stable Y-type zeolite include titanium atoms and further include zirconium atoms or hafnium atoms, or both. The framework-modified ultra-stable Y-type zeolite may be a framework-substituted ultra-stable Y-type zeolite in which aluminum atoms in a framework of the ultra-stable Y-type zeolite are replaced with the heteroatoms. The framework-modified ultra-stable Y-type zeolite may have a crystal lattice constant in a range of 2.430 nanometers (nm) to 2.450 nm.

The acid treatment and the heteroatom incorporation may include preparing a suspension of the ultra-stable Y-type zeolite in water, adding acid to the suspension, and adding a solution (e.g., an aqueous solution) having the heteroatoms to the suspension. The acid may be, for example, sulfuric acid, nitric acid, hydrochloric acid, or carboxylic acids. The solution added may be a first aqueous solution having the titanium atoms and a second aqueous solution having zirconium atoms or hafnium atoms. The acid treatment and heteroatom incorporation may involve neutralizing the suspension to give the framework-modified ultra-stable Y-type zeolite.

The method may include preparing a support of the hydrocracking catalyst. The support may include the framework-modified ultra-stable Y-type zeolite and an inorganic oxide as a granulating agent or binder. The inorganic oxide may include alumina, silica, titania, silica-alumina, alumina-titania, alumina-zirconia, alumina-boria, phosphorus-alumina, silica-alum ina-boria, phosphorus-alumina-boria, phosphorus-alumina-silica, silica-alumina-titania, or silica-alumina-zirconia, or any combinations thereof. The method may include impregnating the support with an active phase metal or hydrogenative metal such that the support carries the active phase metal or the hydrogenative metal. The method may include forming the hydrocracking catalyst with the framework-modified ultra-stable Y-type zeolite in a catalyst support of the hydrocracking catalyst, wherein the framework-modified ultra-stable Y-type zeolite has a specific surface area in a range of 600 m$^2$/g to 900 m$^2$/g.

Another embodiment is a method of producing a hydrocracking catalyst. The method includes preparing a suspension of an ultra-stable Y-type zeolite in a liquid. The ultra-stable Y-type zeolite having an SAR in a range of 3 to 6, or a range of 4 to 6, or in a range of 5 to 6, or an SAR of at least 5. The suspension may have a mass ratio of the liquid to solid in a range of 5 to 15. The liquid in the suspension may include water. The method incudes performing acid treatment on the ultra-stable Y-type zeolite to increase the SAR of the ultra-stable Y-type zeolite. The acid treatment involves adding an acid to the suspension. The method includes adding heteroatoms to the suspension contemporaneous with performing the acid treatment to incorporate the heteroatoms into a framework of the ultra-stable Y-type zeolite to give a framework-substituted ultra-stable Y-type zeolite having an SAR of at least 40. The heteroatoms added to the suspension and incorporated into the framework may include titanium atoms and further include zirconium atoms or hafnium atoms, or both, and wherein to incorporate the heteroatoms into the framework involves to replace aluminum atoms in the framework with the heteroatoms. The framework-substituted ultra-stable Y-type zeolite may have an SAR in a range of 20 to 100, a crystal lattice constant in a range of 2.430 nm to 2.450 nm, and a specific surface area in the range of 600 m$^2$/g to 900 m$^2$/g.

The method includes impregnating a hydrogenative metal on a catalyst support having the framework-substituted ultra-stable Y-type zeolite. The hydrogenative metal may include a metal component having iron, cobalt, nickel, rhodium, palladium, silver, iridium, platinum, gold, chromium, molybdenum, or tungsten, or any combinations thereof. The method includes forming the hydrocracking catalyst with a catalyst support having the framework-substituted ultra-stable Y-type zeolite. The hydrogenative metal may be less than 40% by mass of the hydrocracking catalyst. Lastly to provide the initial ultra-stable Y-type zeolite, the method may include replacing (e.g., via ion exchange and calcination) at least 80% of Na ions in a Y-type zeolite with NH$_4$ ions to give the ultra-stable Y-type zeolite.

Yet another embodiment includes a method of forming a framework-modified ultra-stable Y-type zeolite for a catalyst support of a hydrocracking catalyst. The method includes subjecting an ultra-stable Y-type zeolite having an SAR in a range of 3 to 6 to acid treatment and heteroatom incorporation contemporaneously to give the framework-modified ultra-stable Y-type zeolite having an SAR of at least 20, or at least 30, or at least 40, and a specific surface area of at least 600 m$^2$/g. The method may include preparing a suspension of the ultra-stable Y-type zeolite in water, wherein subjecting the ultra-stable Y-type zeolite to acid treatment and heteroatom incorporation contemporaneously involves mixing acid with the suspension so that a pH of the suspension is less than 2.0, mixing heteroatoms with the suspension, and neutralizing the suspension to give the framework-modified ultra-stable Y-type zeolite. The method may include preparing the catalyst support having the framework-modified ultra-stable Y-type zeolite as a component for the hydrocracking catalyst. The framework-modified ultra-stable Y-type zeolite may have a crystal lattice constant in the range of 2.430 nm to 2.450 nm.

To form the initial ultra-stable Y-type zeolite, the method may include: performing a first ion-exchange on a Y-type zeolite to exchange sodium ions of the Y-type zeolite with ammonium ions to give a first ammonium-exchanged Y-type zeolite; calcining the first ammonium-exchanged Y-type zeolite; performing a second ion-exchange on the first ammonium-exchanged Y-type zeolite as calcined to exchange sodium ions of the first ammonium-exchanged Y-type zeolite as calcined with ammonium ions to give a second ammonium-exchanged Y-type zeolite; and calcining the second ammonium-exchanged Y-type zeolite to give the ultra-stable Y-type zeolite. At least 80% of sodium ions in the Y-type zeolite may be replaced with ammonium ions to give the ultra-stable Y-type zeolite.

A number of implementations have been described. Nevertheless, it will be understood that various modifications may be made without departing from the spirit and scope of the disclosure.

What is claimed is:

1. A method of producing a hydrocracking catalyst for hydrocarbon oil, comprising:
   exchanging at least 80% of sodium (Na) ions in a Y-type zeolite with ammonium (NH$_4$) ions to convert the Y-type zeolite to an ultra-stable Y-type zeolite comprising a silica-to-alumina molar ratio (SAR) in a range of 3 to 6; and
   subjecting the ultra-stable Y-type zeolite comprising the SAR in the range of 3 to 6 to incorporation of heteroatoms and acid treatment simultaneously to give a framework-modified ultra-stable Y-type zeolite comprising an SAR of at least 20, wherein the heteroatoms are incorporated into a framework of the ultra-stable Y-type zeolite, the heteroatoms comprising titanium atoms and further comprising zirconium atoms or hafnium atoms, or both.

2. The method of claim 1, wherein exchanging at least 80% of Na ions in the Y-type zeolite with NH$_4$ ions comprises ion exchange and calcination, and wherein the framework-modified ultra-stable Y-type zeolite is a framework-substituted ultra-stable Y-type zeolite in which aluminum atoms in the framework of the ultra-stable Y-type zeolite are replaced with the heteroatoms.

3. The method of claim 1, wherein the acid treatment and the incorporation of heteroatoms comprise preparing a suspension of the ultra-stable Y-type zeolite in water, adding acid and the heteroatoms to the suspension, and wherein the framework-modified ultra-stable Y-type zeolite comprises an SAR of at least 30.

4. The method of claim 3, wherein the acid comprises sulfuric acid, nitric acid, hydrochloric acid, or carboxylic acids, or any combinations thereof.

5. The method of claim 3, wherein adding the heteroatoms to the suspension comprises adding a first aqueous solution comprising the titanium atoms to the suspension and adding a second aqueous solution comprising zirconium atoms or hafnium atoms, or both, to the suspension.

6. The method of claim 3, wherein the acid treatment and the incorporation of the heteroatoms further comprises neutralizing the suspension to give the framework-modified ultra-stable Y-type zeolite, and wherein the framework-modified ultra-stable Y-type zeolite comprises an SAR in a range of 20 to 100.

7. The method of claim 1, wherein the framework-modified ultra-stable Y-type zeolite comprises an SAR of at least 40 and a crystal lattice constant in a range of 2.430 nanometers (nm) to 2.450 nm.

8. The method of claim 1, comprising preparing a support material to be a catalyst support of the hydrocracking catalyst, the support material comprising the framework-modified ultra-stable Y-type zeolite and an inorganic oxide as a granulating agent or binder.

9. The method of claim 8, wherein the inorganic oxide comprises alumina, silica, titania, silica-alumina, alumina-titania, alumina-zirconia, alumina-boria, phosphorus-alumina, silica-alumina-boria, phosphorus-alumina-boria, phosphorus-alumina-silica, silica-alumina-titania, or silica-alumina-zirconia, or any combinations thereof.

10. The method of claim 8, comprising impregnating the support material with a hydrogenative metal such that the support material carries the hydrogenative metal.

11. The method of claim 1, comprising forming the hydrocracking catalyst with the framework-modified ultra-stable Y-type zeolite in a catalyst support of the hydrocracking catalyst, wherein the framework-modified ultra-stable Y-type zeolite comprises a specific surface area in a range of 600 square meter per gram (m$^2$/g) to 900 m$^2$/g.

12. A method of producing a hydrocracking catalyst, comprising
preparing a suspension of an ultra-stable Y-type zeolite in a liquid, the ultra-stable Y-type zeolite having a silica-to-alumina molar ratio (SAR) in a range of 3 to 6;
performing acid treatment on the ultra-stable Y-type zeolite to increase the SAR of the ultra-stable Y-type zeolite, the acid treatment comprising adding an acid to the suspension;
adding heteroatoms to the suspension simultaneously with performing the acid treatment to incorporate the heteroatoms into a framework of the ultra-stable Y-type zeolite to give a framework-substituted ultra-stable Y-type zeolite having an SAR of at least 20; and
impregnating a hydrogenative metal on a catalyst support comprising the framework-substituted ultra-stable Y-type zeolite.

13. The method of claim 12, wherein the heteroatoms added to the suspension and incorporated into the framework comprise titanium atoms and further comprise zirconium atoms or hafnium atoms, or both, wherein to incorporate the heteroatoms into the framework comprises to replace aluminum atoms in the framework with the heteroatoms, and wherein the framework-substituted ultra-stable Y-type zeolite has an SAR of at least 30.

14. The method of claim 12, comprising replacing at least 80% of sodium (Na) ions in a Y-type zeolite with ammonium (NH$_4$) ions to give the ultra-stable Y-type zeolite, and wherein the framework-substituted ultra-stable Y-type zeolite comprises a specific surface area in the range of 600 square meter per gram (m$^2$/g) to 900 m$^2$/g.

15. The method of claim 14, wherein replacing at least 80% of Na ions in the Y-type zeolite with NH$_4$ ions comprises ion exchange and calcination, wherein the suspension comprises a mass ratio of the liquid to solid in a range of 5 to 15, wherein the liquid in the suspension comprises water, and wherein the framework-substituted ultra-stable Y-type zeolite has an SAR of at least 40.

16. The method of claim 12, wherein the framework-substituted ultra-stable Y-type zeolite comprises a crystal lattice constant in a range of 2.430 nanometers (nm) to 2.450 nm, and wherein the hydrogenative metal is less than 40% by mass of the hydrocracking catalyst.

17. The method of claim 12, comprising forming the hydrocracking catalyst with a catalyst support comprising the framework-substituted ultra-stable Y-type zeolite, and wherein the framework-substituted ultra-stable Y-type zeolite comprises an SAR in a range of 30 to 100.

18. The method of claim 12, wherein the hydrogenative metal comprises a metal component comprising iron, cobalt, nickel, rhodium, palladium, silver, iridium, platinum, gold, chromium, molybdenum, or tungsten, or any combinations thereof.

19. A method of forming a framework-modified ultra-stable Y-type zeolite for a catalyst support of a hydrocracking catalyst, comprising:
subjecting an ultra-stable Y-type zeolite having a silica-to-alumina molar ratio (SAR) in a range of 3 to 6 to incorporation of heteroatoms and acid treatment simultaneously to give the framework-modified ultra-stable Y-type zeolite; and
wherein the framework-modified ultra-stable Y-type zeolite comprises an SAR of at least 30 and a specific surface area of at least 600 square meter per gram (m$^2$/g).

20. The method of claim 19, comprising:
performing a first ion-exchange on a Y-type zeolite to exchange sodium ions of the Y-type zeolite with ammonium ions to give a first ammonium-exchanged Y-type zeolite;
calcining the first ammonium-exchanged Y-type zeolite;
performing a second ion-exchange on the first ammonium-exchanged Y-type zeolite as calcined to exchange sodium ions of the first ammonium-exchanged Y-type zeolite as calcined with ammonium ions to give a second ammonium-exchanged Y-type zeolite; and
calcining the second ammonium-exchanged Y-type zeolite to give the ultra-stable Y-type zeolite.

21. The method of claim 20, wherein at least 80% of sodium ions in the Y-type zeolite are replaced with ammonium ions, and wherein the framework-modified ultra-stable Y-type zeolite comprises a crystal lattice constant in the range of 2.430 nanometers (nm) to 2.450 nm.

22. The method of claim 19, comprising preparing a suspension of the ultra-stable Y-type zeolite in water, wherein subjecting the ultra-stable Y-type zeolite to acid treatment and incorporation of the heteroatoms simultaneously comprises mixing acid and the heteroatoms with the suspension so that a pH of the suspension is less than 2.0, and neutralizing the suspension to give the framework-modified ultra-stable Y-type zeolite.

23. The method of claim 19, comprising preparing the catalyst support having the framework-modified ultra-stable Y-type zeolite as a component for the hydrocracking catalyst, wherein the framework-modified ultra-stable Y-type zeolite comprises an SAR of at least 40.

* * * * *